United States Patent [19]

Welch, Jr. et al.

[11] 4,006,164
[45] Feb. 1, 1977

[54] 4-ARYL-1,2,3,4-TETRAHYDROPYR-ROLO[3,4-b]INDOLES

[75] Inventors: Willard M. Welch, Jr., North Stonington; Charles A. Harbert, Waterford, both of Conn.

[73] Assignee: Pfizer Inc., New York, N.Y.

[22] Filed: June 23, 1975

[21] Appl. No.: 589,384

Related U.S. Application Data

[62] Division of Ser. No. 456,641, April 1, 1974, Pat. No. 3,925,409.

[52] U.S. Cl. .................. 260/326.5 B; 260/326.25; 260/326.5 J; 260/326.62; 260/326.9; 424/274
[51] Int. Cl.$^2$ ..................................... C07D 487/04
[58] Field of Search ................. 260/326.9, 326.5 B
[56] References Cited
UNITED STATES PATENTS

| 3,553,232 | 1/1971 | Hester | 260/326.5 B |
| 3,652,588 | 3/1972 | Hester | 260/326.5 B |
| 3,925,409 | 12/1975 | Welch, Jr. et al. | 260/326.9 |
| 3,968,231 | 7/1976 | Welch et al. | 424/274 |

FOREIGN PATENTS OR APPLICATIONS

| 1,183,093 | 3/1970 | United Kingdom | 260/326.5 B |

OTHER PUBLICATIONS

Southwich et al., J. Org. Chem. vol. 25, p. 1123 (1960).

Primary Examiner—Donald G. Daus
Assistant Examiner—Mary Vaughn
Attorney, Agent, or Firm—Connolly and Hutz

[57] ABSTRACT

2-Substituted-4-aryl-1,2,3,4-tetrahydropyrrolo[3,4-b]-indoles, their use as tranquilizing agents and their preparation from 4-aryl-1,2,3,4-tetrahydropyrrolo[3,4-b]indoles.

3 Claims, No Drawings

4-ARYL-1,2,3,4-TETRAHYDROPYRROLO[3,4-B]INDOLES

CROSS REFERENCE TO RELATED APPLICATION

This application is a division of application Ser. No. 456,641 filed Apr. 1, 1974 and now U.S. Pat. No. 3,925,409.

BACKGROUND OF THE INVENTION

Following the introduction of reserpine and chlorpromazine in psychotherapeutic medicine in the early 1950's, great effort has been expended in the search for other tranquilizing agents having improved biological profiles.

It has now been found certain indoles, and more particularly a series of 2-substituted-4-aryl-1,2,3,4-tetrahydropyrrolo[3,4-b]indoles, are extremely effective as tranquilizing agents.

The fused pyrrolo[3,4-b]indole ring system is relatively new in the chemical literature, the first successful preparation being reported by Southwich, et al., *J. Org. Chem.*, 25, 1123 (1960). These simple 2-substituted-1,2,3,4-tetrahydropyrrolo[3,4-b]indoles failed to demonstrate the antitumor activity for which they were prepared and tested.

SUMMARY OF THE INVENTION

The tranquilizing agents of this invention are represented by the formula

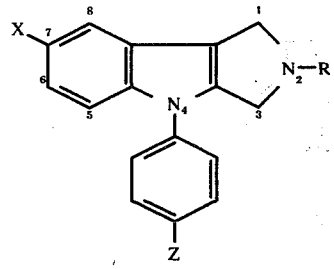

and the pharmaceutically acceptable acid addition salts thereof, wherein X is fluoro, chloro, bromo, methyl or hydrogen, Z is fluoro, chloro, methoxy or hydrogen; and R is alkyl containing from 1 to 6 carbon atoms, benzyl or substituted alkylene of the formula

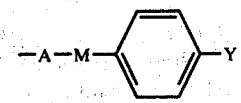

wherein A is alkylene containing from 1 to 5 carbon atoms, M is —CH=CH—, —CH$_2$—,

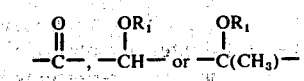

wherein R$_1$ is hydrogen or alkanoyl containing from 2 to 5 carbon atoms and Y is fluoro, chloro, methyl or hydrogen.

The compounds of the present invention of the formula

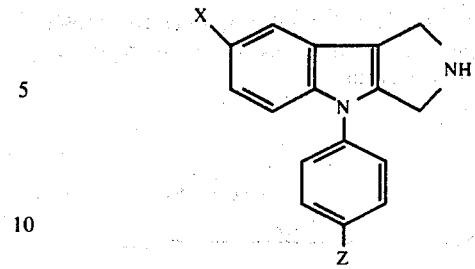

wherein X and Z are as previously indicated are useful intermediates leading to the tranquilizers of the preset invention.

A preferred group of chemotherapeutic compounds of the instant invention are those of formula I wherein X is fluoro, Z is fluoro, chloro, hydrogen or methoxy and R is substituted alkylene of the formula

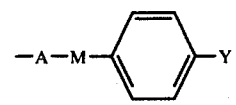

wherein A is alkylene containing 1 to 5 carbon atoms, M is

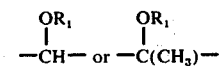

wherein R$_1$ is hydrogen or alkanoyl containing from 2 to 5 carbon atoms and Y is fluoro, chloro, methyl or hydrogen.

A preferred class of intermediate compounds of the formula

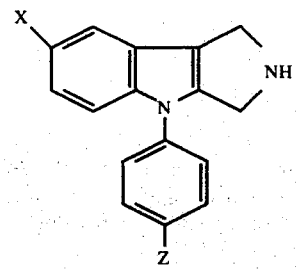

are those wherein X is fluoro and Z is fluoro, chloro, methoxy and hydrogen.

Also considered within the purview of the present invention are congeners of the formula

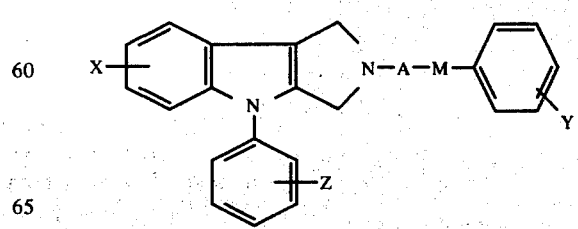

wherein X, Y, Z, M and A are as previously defined.

DETAILED DESCRIPTION OF THE INVENTION

In accordance with the process employed for synthesizing the compounds of the present invention the following scheme is illustrative:

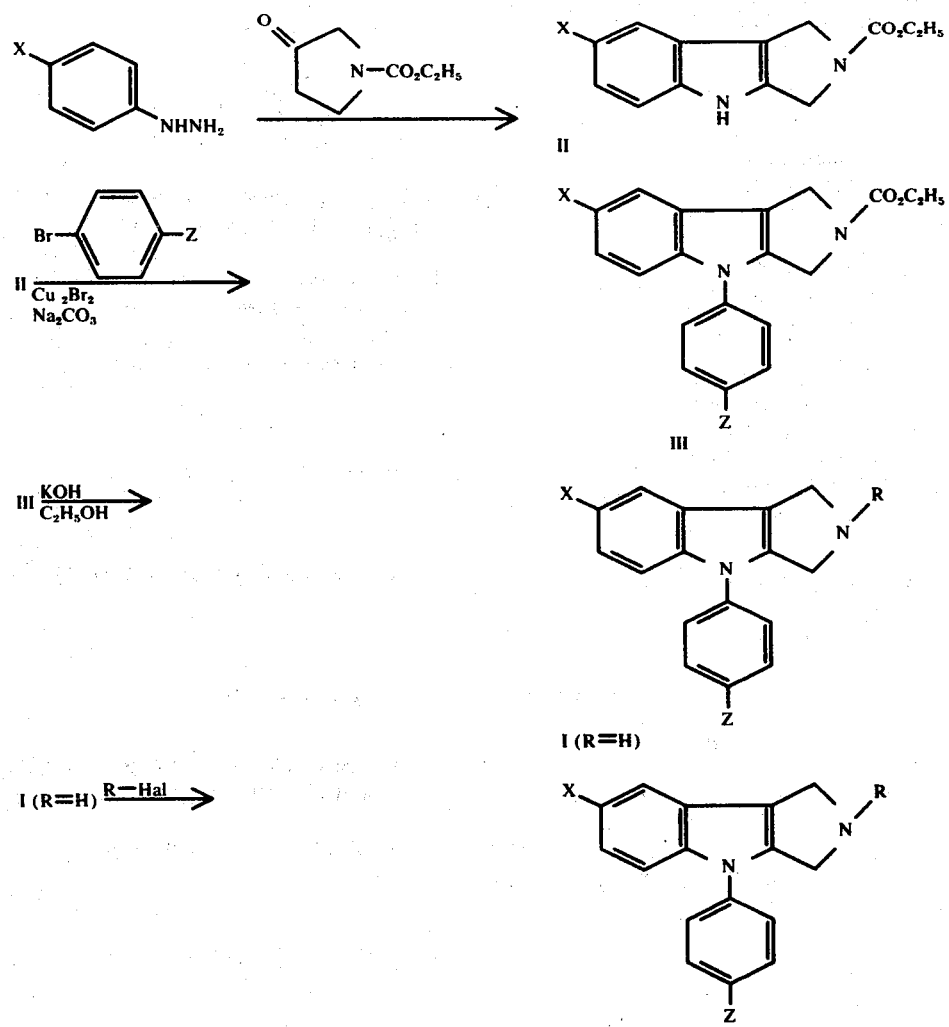

wherein X and Z are as previously defined, Hal is a halogen and R is hydrogen, benzyl, alkyl having 1 to 6 carbon atoms or substituted alkylene of the formula

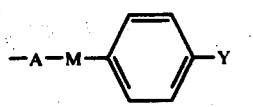

wherein A is alkylene having 1 to 5 carbon atoms, M is —CH$_2$— or

and Y is as previously defined.

In practice, the pyrrolo[3,4-b]indoles of formula II are conveniently prepared from 1-carbethoxy-3-pyrrolidinone, prepared by the method of Kuhn, Chem. Ber., 89, 1423 (1956) or Viscontini, Helv. Chim. Acta., 50, 1289 (1967), and the requisite phenyl hydrazine by the classical Fischer indole synthesis which comprises contacting the appropriate hydrazone, formed from the hydrazine and pyrrolidinone reagents, with an acid catalyst such as phosphoric acid.

Arylation of II is effected through the reaction of II with a suitably substituted p-bromobenzene derivative, employing a 2-3 fold molar excess of the bromobenzene derivative for optimum yields of the product, III. In addition, equimolar amounts, plus as much as a 100% excess, of cuprous bromide and sodium carbonate are employed in this reaction, said reaction being conducted in a reaction-inert solvent such as nitrobenzene, hexamethylphosphoramide or N-methyl-2-pyrrolidione at a temperature of 125°–225° C. with a preferred range of 175°–200° C.

Hydrolysis of compounds related to III is effected by heating an ethanol solution of the appropriate 2-carbethoxy-4-aryl-1,2,3,4-tetrahydropyrrolo[3,4-b]indole with at least two molar equivalents of potassium hydroxide.

This sequence of reactions is preferred for the preparation of the useful intermediates of the instant invention of formula I, where R represents hydrogen.

Compounds of formula I wherein X and Z are previously described and R is alkyl, benzyl or substituted alkylene of the formula

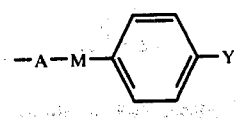

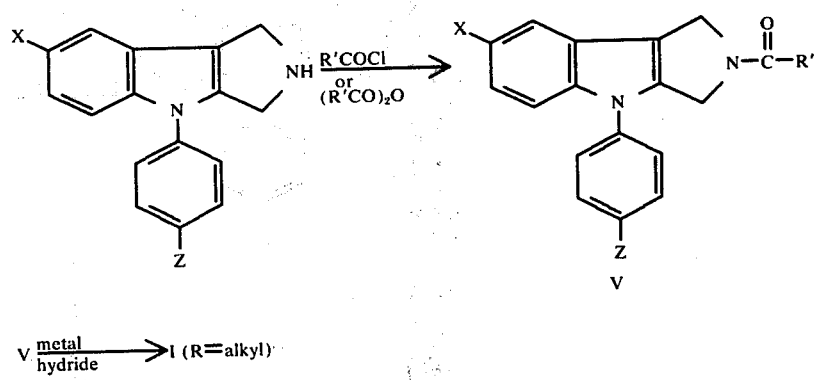

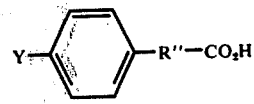

where A is alkylene, M is —$CH_2$— or $$-\overset{O}{\underset{\|}{C}}-$$

and Y is as previously defined are synthesized by alkylation of I wherein R is hydrogen.

Experimentally, the reaction is conducted with an equimolar amount, plus as much as a 10–20% excess, of the alkylating agent in a reaction-inert, aprotic, polar solvent, such as dimethylformamide, tetramethylenesulfone, dimethylsulfoxide, hexamethylphosphoramide or a dialkyl ketone, at elevated temperatures. To facilitate the completion of the reaction a catalytic amount of potassium iodide is added to the reaction mixture, forming in situ reactive amounts of the iodo alkylating agent. In addition, a two to three mole excess of sodium carbonate is added as a scavenger for the hydrogen halide produced as a by-product in said alkylation.

Several additional synthetic pathways can be employed in the preparation of compounds of formula I, wherein R is alkyl. The first alternate route employs the use of the initial reaction of a phenylhydrazine derivative with a 1-alkyl-3-pyrrolidinone followed by arylation of the 4-position; this reaction scheme is illustrated as follows:

The second alternate synthetic scheme leading to 2-alkyl-4-aryl-1,2,3,4-tetrahydropyrrolo[3,4-b]indoles employs acylation of compounds of formula I wherein R is hydrogen with an appropriate acid halide, anhydride or mixed anhydride, followed by a metal hydride reduction of the formed amide, according to the following illustrative route:

wherein X and Z are as previously defined and R' is alkyl containing from 1 to 5 carbon atoms.

In practice, the acylation of compounds of formula I (R = H), shown above, is effected with an acid halide, anhydride or mixed anhydride employing equimolar amounts of the acylating agent plus as much as a 20% excess in a reaction-inert solvent such as a chlorinated hydrocarbon. An equimolar amount, plus as much as a two-fold excess, of a tertiary amine, such as triethyl amine, is added to facilitate the completion of the reaction, which can be conducted at ambient temperatures.

Reduction of compounds of formula V is most conveniently achieved employing a metal hydride such as lithium aluminum hydride or aluminum hydride in a reaction-inert solvent such as one of the dialkyl or cycloalkyl ethers.

Similarly, acylation can be carried out with the corresponding acid halide or anhydride of an aralkanoic acid of the formula:

wherein Y is as previously defined and R'' is alkylene

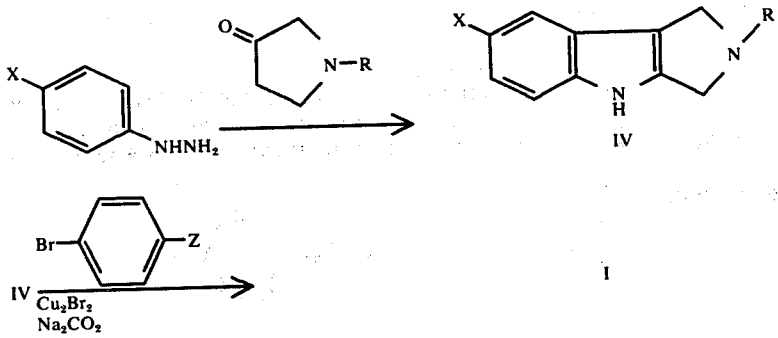

The conditions of the Fischer indole synthesis leading to IV and the subsequent arylation reaction of IV leading to I are similar to those previously described.

of from 1 to 5 carbon atoms.

Reduction of the formed amides, similar to V, is effected using lithium aluminum hydride or aluminum hydride and provides compounds wherein the 2-substituent is aralkyl of the formula

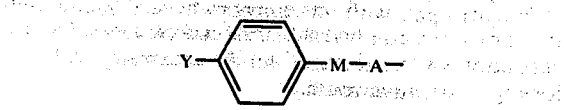

wherein X, M and A are as defined.

A third synthetic pathway to compounds of formula I where R is methyl comprises a lithium aluminum hydride reduction of compounds of formula III as follows

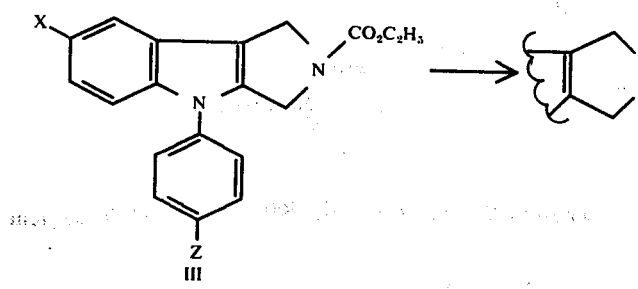

As one skilled in the art can readily appreciate, any carbalkoxy can be employed in this route leading to the 2-methyl congeners.

An alternate preparative route leading to compounds of formula I wherein R is

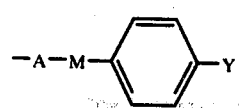

where A and X are as previously defined and M is

is shown in the following flow diagram:

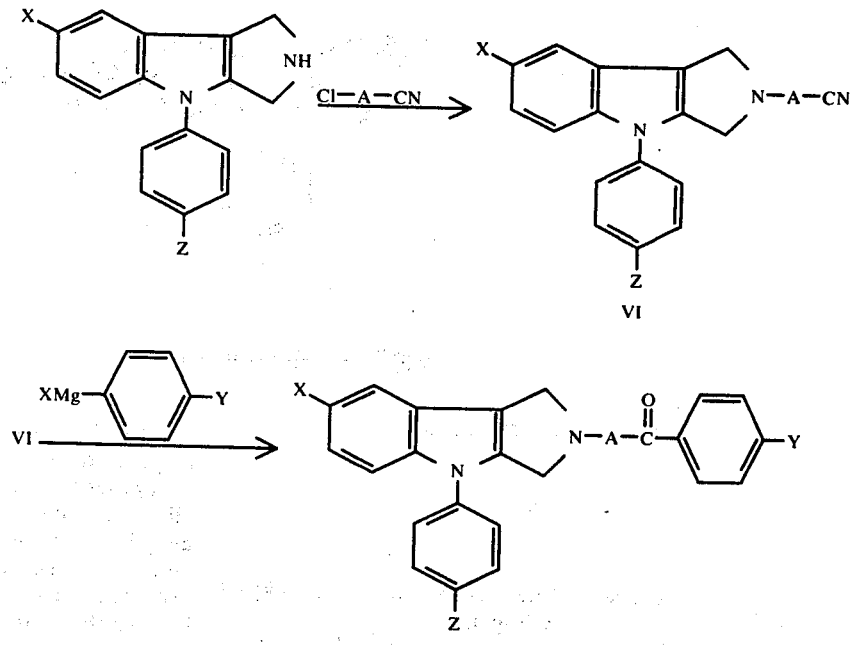

Alkylation of compounds of formula I (R = H) with an ω-haloalkyl nitrile is effected under the same alkylation conditions previously described.

Further reaction of the nitrile, VI, with the requisite Grignard reagent leads to the described ketones. It is preferred that four moles of Grignard reagent per mole of nitrile be employed, although the desired product can be prepared with less of an excess. As with Grignard reactions, it is preferred that the reaction be conducted in a reaction-inert solvent such as diethyl ether.

Synthesis of compounds for formula I wherein R is

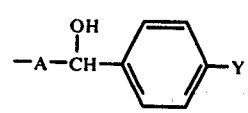

wherein A and Y are as previously defined are effected by reduction of the corresponding ketone employing sodium borohydride as illustrated in the following scheme:

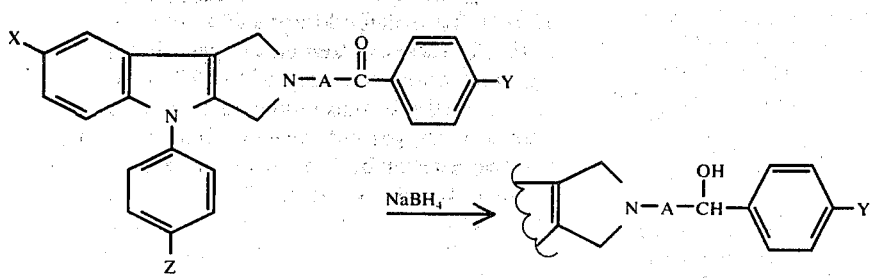

Experimentally, one mole of ketone is contacted with approximately four moles of the hydride in a reaction-inert solvent, such as ethanol, at elevated temperatures. The addition of tetrahydrofuran facilitates the reaction by enhancing the solubility of the reactants.

The tertiary alcohols of the present invention are prepared by the reaction of the appropriate ketone with methyl magnesium iodide, illustrated as follows:

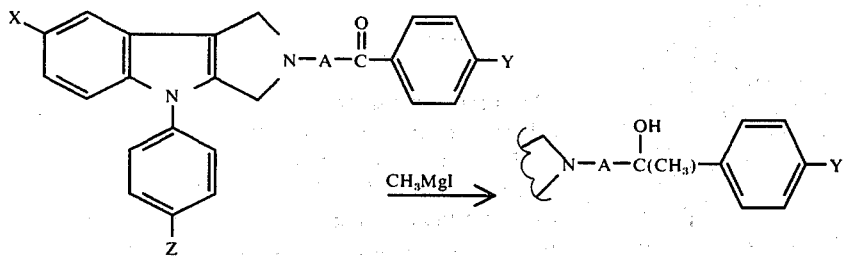

where X, Z, A and Y are as previously defined.

As in the previously described Grignard reaction, although the starting materials react in equimolar amounts, it is preferred that as much as a 100% excess of the methyl magnesium iodide be employed. In addition, it is also preferred that the reaction be conducted in a reaction-inert solvent such as diethyl ether at ambient temperatures.

The alcohols of the present invention are readily converted to esters by acylation with an acid halide, anhydride or mixed anhydride. These acylation reactions can be conducted in such solvents as chlorinated hydrocarbons employing a tertiary amine, such as pyridine or triethyl amine, to ensure completeness of the reaction.

The secondary alcohols of the instant invention, on treatment with 6N hydrochloric acid at elevated temperatures, are converted by dehydration to those congeners wherein M is —CH=CH—. It is frequently preferred that a cosolvent such as ethanol be employed in order to enhance the solubility of the pyrrolo[3,4-b]indole.

Regarding the requisite starting reagents leading to the synthesis of the compounds of the instant invention, they are either commercially available, their preparation is explicitly reported in the chemical literature or they can be prepared by methods known to those skilled in the art. For example, the phenylhydrazines are commercially available or are synthesized by reduction of the phenyldiazonium salt as taught by Wagner and Zook, "Synthetic Organic Chemistry," John Wiley and Sons, New York, N.Y., 1956, Chapter 26; the ω-haloalkyl aryl ketones are prepared by the method described in U.S. Pat. No. 2,997,472 (C.A. 56, 11603 [1962]); and the 1-alkyl-3-pyrrolidinones are synthesized as taught by Casy, et al., J. Pharm. Pharmacol. 17(3), 157 (1965).

As has been previously mentioned, the compounds of the present invention can form acid addition salts. Said basic compounds are converted to their acid addition salts by interaction of the base with an acid either in an aqueous or nonaqueous medium. In a similar manner, treatment of the acid addition salts with an equivalent amount of an aqueous base solution, e.g., alkali metal hydroxides, alkali metal carbonates and alkali metal bicarbonates or with an equivalent amount of a metal cation which forms an insoluble precipitate with the acid anion, results in the regeneration of the free base form. The bases thus regenerated may be reconverted to the same or a different acid addition salt.

In the utilization of the chemotherapeutic activity of those compounds of the present invention, it is preferred, of course, to use pharmaceutically acceptable salts. Although water-insolubility, high toxicity, or lack of crystalline nature may make some particular salt species unsuitable or less desirable for use as such in a given pharmaceutical application, the water insoluble or toxic salts can be converted to the corresponding pharmaceutically acceptable bases by decomposition of the salt as described above, or alternately, they can be converted to any desired pharmaceutically acceptable acid addition salt.

Examples of acids which provide pharmaceutically acceptable anions are hydrochloric, hydrobromic, hydroiodic, nitric, sulfuric, or sulfurous, phosphoric, acetic, lactic, citric, tartaric, succinic, maleic and gluconic acids.

As previously indicated, the pyrrolo[3,4-b]indoles of the present invention are, with the exception of those compounds of formula I wherein R is hydrogen, said compounds being useful as intermediates, are readily adapted to therapeutic use as tranquilizing agents in mammals. Outstanding for their effectiveness in this regard include the following agents: 7-fluoro-4-(p-fluorophenyl)-2-[4-(p-fluorophenyl)-4-hydroxybutyl]-1,2,3,4-tetrahydropyrrolo-[3,4-b]indole, 7-fluoro-4-(p-fluorophenyl)-2-[4-(p-fluorophenyl)-4-acetoxybutyl]-1,2,3,4-tetrahydropyrrolo[3,4-b]indole, 7- fluoro-4-(p-fluorophenyl)-2-[4-(p-fluorophenyl)-4-hydroxypenytyl]-1,2,3,4-tetrahydropyrrolo[3,4-b]indole and 7-fluoro-4-(p-fluorophenyl)-2-[4-(p-fluorophenyl)-4-acetoxypentyl]-1,2,3,4-tetrahydropyrrolo[3,4-b]indole. The preferred intermediate compound of the present invention is 7-fluoro-4-(p-fluorophenyl)-1,2,3,4-tetrahydropyrrolo-[3,4-b]indole.

The tranquilizing agents of the present invention are characterized by relief of such schizophrenic manifestations in humans as hallucinations, hostility, suspiciousness, emotional and social withdrawal, anxiety, agitation and tension. Standard procedures of detecting and comparing tranquilizing activity of compounds in this series and for which there is an excellent correlation with human efficacy is the antagonism of amphetamine-induced symptoms in rats test as taught by A. Weissman, et al., *J. Pharmacol. Exp. Ther.*, 151, 339 (1966) and by Quinton, et al., Nature, 200, 178 (1963).

The pyrrolo[3,4-b]indoles and the pharmaceutically acceptable salts thereof, which are useful as tranquilizers, can be administered either as individual therapeutic agents or as mixtures of therapeutic agents. They may be administered alone, but are generally administered with a pharmaceutical carrier selected on the basis of the chosen route of administration and standard pharmaceutical practice. For example, they can be administered orally in the form of tablets or capsules containing such excipients as starch, milk sugar, or certain types of clay, etc. They can be administered in the form of elixirs or oral suspensions with the active ingredients combined with emulsifying and/or suspending agents. They may be injected parenterally, and for this use they, or appropriate derivatives, may be prepared in the form of sterile aqueous solutions. Such aqueous solutions should be suitably buffered, if necessary, and should contain other solutes such as saline or glucose to render them isotonic.

Although the use of the present invention is directed toward the treatment of mammals in general, the preferred subject is humans. In determining an efficacious dose for human therapy, results of animal testing are frequently extrapolated and a correlation is assumed between animal test behavior and proposed human dosage. When a commercially employed standard is available, the dose level of the clinical candidate in humans is frequently determined by comparison of its performance with the standard in an animal test. For example, if a standard tranquilizing agent is administered effectively to humans at the rate of 100 to 400 mg. daily, it is assumed, then, that if the compounds of the present invention have activity comparable to this standard in the test assay, that similar doses will provide comparable responses in humans.

Obviously the physician will ultimately determine the dosage which will be most suitable for a particular individual, and it will vary with age, weight and response of the particular patient, as well as with the nature and extent of the symptoms and the pharmacodynamic characteristics of the particular agent to be administered. Generally, small doses will be administered initially, with a gradual increase in the dosage until the optimum level is determined. It will often be found that when the composition is administered orally, larger quantities of the active ingredient will be required to produce the same level as produced by a smaller quantity administered parenterally.

Having full regard for the foregoing factors, it is considered that a daily dosage of the compounds of the instant invention in humans of approximately 1 to 100 mg., with a preferred range of 1 to 50 mg., will tranquilize effectively. In those individuals in which the compounds of the present invention have a prolonged effect, the dose can be 5 to 150 mg. a week, administered in one or two divided doses. These values are illustrative, and there may, of course, be individual cases where higher or lower dose ranges are merited.

The following examples are provided solely for the purpose of illustration and are not to be construed as limitations of this invention, many variations of which are possible without departing from the spirit or scope thereof.

EXAMPLE 1

7-Fluoro-4-(p-fluorophenyl)-1,2,3,4-tetrahydropyrrolo[3,4-b]indole hydrochloride (I: X and Z = F and R = H)

A.

7-fluoro-2-carbethoxy-1,2,3,4-tetrahydropyrrolo[3,4-b]indole (II: X = F)

To a stirring suspension of 5.67 g. (0.035 mole) of p-fluorophenyl hydrazine hydrochloride and 2.87 g. (0.035 mole) of sodium acetate in 200 ml. of water is added dropwise 5.5 g. (0.035 mole) of 1-carbethoxy-3-pyrrolidinone in 50 ml. of the same solvent. After stirring for 20 min., the precipitated hydrazone is filtered, washed with water and dried, 9.0 g. The analytical sample is recrystallized from methylene chloride-hexane, m.p. 157°–160° C.

To 3.9 g. (14.7 m moles) of the above hydrazone is added 25 ml. of 85% phosphoric acid, the mixture becoming mildly exothermic as the solid dissolves. Within 30 min. the mixture sets-up to a semisolid, which is treated with an additional 10 ml. of phosphoric acid and allowed to stir until a uniform brown suspension results. The reaction mixture is quenched with 200 ml. of cold water, and the resulting precipitate is filtered and dried, 2.19 g. Recrystallization from ethanol-water provided 1.4 g. of the desired product, m.p. 248°–249° C.

Anal. Calc'd for $C_{13}H_{13}O_2N_2F$: C, 62.9; H, 5.2; N, 11.3. Found: C, 62.9; H, 5.3; N, 11.5.

B.

7-fluoro-4-(p-fluorophenyl)-2-carbethoxy-1,2,3,4-tetrahydropyrrolo[3,4-b]indole (III: X and Z = F)

A mixture of 6.6 g. (0.028 mole) of 7-fluoro-2-carbethoxy-1,2,3,4-tetrahydropyrrolo[3,4-b]indole, 8.86 g. (0.031 mole) of cuprous bromide, 3.28 g. (0.031 mole) of sodium carbonate and 17.2 g. (0.098 mole) of p-bromofluorobenzene in 75 ml. of N-methyl-2-pyrrolidione is heated to reflux for 4 hrs. The reaction mixture is cooled and poured into ice and water containing 40 ml. of ethylene diamine. The mixture is extracted with benzene, and the benzene extracts subsequently back-washed with water and a saturated brine solution and dried over magnesium sulfate. Removal of the solvent in vacuo provides a gum which on trituration with hexane provides 5.8 g. of product as a brown solid, m.p. 143°–145° C.

C.
7-fluoro-4-(p-fluorophenyl)-1,2,3,4-tetrahydropyrrolo[3,4-b]indole hydrochloride (I: X and Z = F and R = H)

7-Fluoro-4-(p-fluorophenyl)-2-carbethoxy-1,2,3,4-tetrahydropyrrolo-[3,4-b]indole (342 mg.; 0.001 mole) and 1.12 g. (0.02 mole) of potassium hydroxide in 20 ml. of ethanol and 2 ml. of water is heated to reflux for 24 hrs. followed by evaporation of the solution to a brown gum. The residue is partitioned between methylene chloride and water, and the organic phase separated, washed with water and dried over magnesium sulfate. Removal of the solvent provides the product as a tan solid, which on dissolution in diethyl ether and treatment with an ether solution of hydrogen chloride provides 193 mg. of the hydrochloride salt, m.p. 145°–150° C.

EXAMPLE 2

Starting with the appropriate phenylhydrazines and employing the procedure of Example 1, the following 4-aryl-1,2,3,4-tetrahydropyrrolo[3,4-b]indoles are prepared as the free base and hydrochloride salts: 7-chloro-4-(p-fluorophenyl)-1,2,3,4-tetrahydropyrrolo[3,4-b]indole; 7-bromo-4-phenyl-1,2,3,4-tetrahydropyrrolo[3,4-b]indole; 7-methoxy-4-(p-fluorophenyl)-1,2,3,4-tetrahydropyrrolo[3,4-b]indole; 7-fluoro-4-(p-methoxyphenyl)-1,2,3,4-tetrahydropyrrolo[3,4-b]indole; 7-methyl-4-phenyl-1,2,3,4-tetrahydropyrrolo[3,4-b]indole; 7-fluoro-4-(p-chlorophenyl)-1,2,3,4-tetrahydropyrrolo[3,4-b]indole; 7-fluoro-4-phenyl-1,2,3,4-tetrahydropyrrolo[3,4-b]indole; 7-chloro-4-phenyl-1,2,3,4-tetrahydropyrrolo[3,4-b]indole; 7-chloro-4-(p-chlorophenyl)-1,2,3,4-tetrahydropyrrolo[3,4-b]indole; 7-bromo-4-(p-fluorophenyl)-1,2,3,4-tetrahydropyrrolo[3,4-b]indole; 7-methyl-4-(p-chlorophenyl)-1,2,3,4-tetrahydropyrrolo[3,4-b]indole; 4-phenyl-1,2,3,4-tetrahydropyrrolo[3,4-b]indole; 4-(p-fluorophenyl)-1,2,3,4-tetrahydropyrrolo[3,4-b]indole; 4-(p-chlorophenyl)-1,2,3,4-tetrahydropyrrolo[3,4-b]indole; and 7-chloro-4-(p-methoxyphenyl)-1,2,3,4-tetrahydropyrrolo[3,4-b]indole.

EXAMPLE 3

7-Fluoro-4-(p-fluorophenyl)-2-methyl-1,2,3,4-tetrahydropyrrolo[3,4-b]indole (I: X and Z = F and R = CH$_3$)

To a mixture of 244 mg. (6.4 m moles) of lithium aluminum hydride in 20 ml. of dry tetrahydrofuran under a nitrogen atmosphere and cooled to −10° C. is added 284 mg. (2.1 m moles) of aluminum chloride and the resulting reaction mixture allowed to stir for 30 min. 7-Fluoro-4-(p-fluorophenyl)-2-carbethoxy-1,2,3,4-tetrahydropyrrolo[3,4-b]indole (2.9 m moles) in 10 ml. of the same solvent is added dropwise to the cold solution with stirring. After one hour, the reaction is quenched with 5 ml. of water added dropwise, and the mixture allowed to warm to room temperature. The mixture is filtered and the solids washed with hot tetrahydrofuran. The combined filtrate and washings are concentrated to a brown solid, which on dissolution in diethyl ether followed by treatment with ether saturated with hydrogen chloride provides 448 mg. of the desired product, m.p. 160°–165° C.

EXAMPLE 4

Employing the procedure of Example 3, and starting with the requisite 4-aryl-2-carbethoxy-1,2,3,4-tetrahydropyrrolo[3,4-b]indole, the following analogs are prepared:

| X | Z |
|---|---|
| Cl— | F— |
| Br— | H— |
| CH$_3$O— | F— |
| F— | CH$_3$O— |
| CH$_3$— | F— |
| CH$_3$— | H— |
| F— | Cl— |
| F— | H— |
| Cl— | H— |
| Cl— | Cl— |
| Br— | F— |
| CH$_3$— | Cl— |
| H— | H— |
| H— | F— |
| H— | Cl— |
| Cl— | CH$_3$O— |

EXAMPLE 5

7-Fluoro-4-(p-fluorophenyl)-2-[3-(p-fluorobenzoyl)propyl]-1,2,3,4-tetrahydropyrrolo[3,4-b]indole hydrochloride (I: X and Z = F; A = —(CH$_2$)$_3$—; M = —C(=O)— and Y = F).

7-Fluoro-4-(p-fluorophenyl)-1,2,3,4-tetrahydropyrrolo[3,4-b]indole (6.02 g.; 22.2 m moles), 6.7 g. (33.3 m moles) of γ-chloro-p-fluorobutyrophenone, 4.28 g. (23.4 m moles) of potassium iodide and 7.05 g. (66.6 m moles) of sodium carbonate in 175 ml. of dimethylformamide is heated to 90° C. for 8 hrs. and then allowed to stir at room temperature overnight. The mixture is heated again to 90° C., treated with a gram of decolorizing charcoal, filtered, and the filtrate poured into ice and water. The suspension is extracted with chloroform and the combined extracts dried and evaporated to 10.5 g. of crude product. The residue is chromatographed on 200 g. of silica gel using 3:1 diethyl ether-ethanol as the eluate, each fraction comprising 30–40 ml. The desired product, isolated from fractions 6–14, is converted to the hydrochloride salt, 1.76 g., and subsequently recrystallized from acetonitrile-methanol, 850 mg., m.p. 175°–179° C.

Anal. Calc'd for C$_{26}$H$_{21}$ON$_2$F$_3$·HCl: C, 66.3; H, 4.7; N, 6.0. Found: C, 65.3; H, 4.7; N, 5.8. Mass Spectra Calc'd M$^+$ (free base): 434. Found: 434.

EXAMPLE 6

The procedure of Example 5 is repeated, starting with the requisite ω-haloalkyl aryl ketone and 4-aryl- 1,2,3,4-tetrahydropyrrolo[3,4-b]indole from Examples 1 or 2, to give the following congeners:

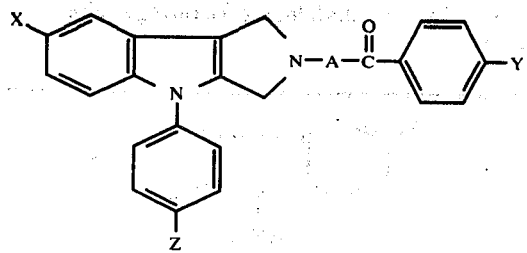

| X | Z | A | Y |
|---|---|---|---|
| F— | F— | —(CH₂)₂— | F— |
| F— | F— | —(CH₂)₄— | F— |
| F— | F— | —(CH₂)₃— | H— |
| F— | F— | —(CH₂)₃— | CH₃— |
| F— | F— | —(CH₂)₃— | Cl— |
| F— | CH₃O— | —(CH₂)₃— | F— |
| F— | F— | —(CH₂)₅— | F— |
| F— | F— | —CH₂— | Cl— |
| F— | Cl— | —(CH₂)₃— | F— |
| F— | Cl— | —(CH₂)₃— | Cl— |
| F— | Cl— | —(CH₂)₃— | CH₃— |
| F— | OCH₃— | —(CH₂)₂— | F— |
| F— | OCH₃— | —(CH₂)₂— | H— |
| F— | OCH₃— | —(CH₂)₅— | Cl— |
| F— | H— | —(CH₂)₃— | F— |
| Cl— | F— | —(CH₂)₃— | F— |
| Cl— | F— | —CH₂— | Cl— |
| Cl— | F— | —(CH₂)₃— | Cl— |
| Cl— | F— | —(CH₂)₃— | CH₃— |
| Cl— | H— | —(CH₂)₃— | F— |
| Cl— | H— | —(CH₂)₅— | F— |
| Cl— | Cl— | —(CH₂)₃— | F— |
| Cl— | OCH₃— | —(CH₂)₃— | F— |
| Cl— | OCH₃— | —(CH₂)₃— | CH₃— |
| Br— | H— | —(CH₂)₃— | F— |
| Br— | H— | —(CH₂)₃— | H— |
| Br— | H— | —(CH₂)₄— | F— |
| Br— | OCH₃— | —(CH₂)₂— | F— |
| Br— | OCH₃— | —(CH₂)₅— | F— |
| Br— | F— | —(CH₂)₃— | F— |
| Br— | Cl— | —(CH₂)₂— | F— |
| CH₃— | Cl— | —(CH₂)₃— | CH₃— |
| CH₃— | Cl— | —(CH₂)₅— | H— |
| CH₃— | F— | —(CH₂)₅— | F— |
| CH₃— | OCH₃— | —(CH₂)₃— | F— |
| CH₃— | OCH₃— | —(CH₂)₄— | F— |
| CH₃— | H— | —(CH₂)₃— | CH₃— |
| H— | OCH₃— | —(CH₂)₃— | F— |
| H— | OCH₃— | —(CH₂)₃— | Cl— |
| H— | OCH₃— | —(CH₂)₂— | CH₃— |
| H— | OCH₃— | —(CH₂)₅— | H— |
| H— | Cl— | —(CH₂)₃— | F— |
| H— | Cl— | —(CH₂)₅— | H— |

EXAMPLE 7

7-Fluoro-4-(p-fluorophenyl)-2-[4-(p-fluorophenyl)-4-hydroxybutyl]-1,2,3,4-tetrahydropyrrolo[3,4-b]indole hydrochloride (I: X and Z = F; A = —(CH₂)₃—; M = —CH(OH)— and Y = F)

To a solution of 2.4 g. (5.5 m moles) of 7-fluoro-4-(p-fluorophenyl)-2-[3-(p-fluorobenzoyl)propyl]-1,2,3,4-tetrahydropyrrolo[3,4-b]indole in 85 ml. of dry tetrahydrofuran containing 12 ml. of ethanol is added portionwise 1.2 g. of sodium borohydride over a period of 2 hrs. The brownish solution is then evaporated to dryness and partitioned between water and diethyl ether. The organic layer is separated, dried over magnesium sulfate and concentrated in vacuo to dryness. The residual product, after it is converted to the hydrochloride salt, is recrystallized from acetonitrile to give 430 mg. of pure product, m.p. 210°–211.5° C. A second crop is isolated from the filtrate, 290 mg., m.p. 203°–205° C.

EXAMPLE 8

The reduction procedure of Example 7 is repeated, starting with the appropriate ketones from Examples 5 or 6, to give the following carbinols:

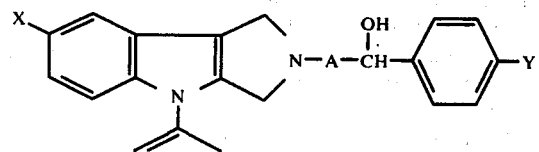

| X | Z | A | Y |
|---|---|---|---|
| F— | CH₃O— | —(CH₂)₃— | F— |
| F— | F— | —(CH₂)₃— | CH₃— |
| F— | F— | —(CH₂)₃— | Cl— |
| F— | F— | —(CH₂)₂— | F— |
| F— | F— | —(CH₂)₄— | F— |
| F— | F— | —(CH₂)₅— | F— |
| F— | F— | —CH₂— | Cl— |
| F— | Cl— | —(CH₂)₃— | F— |
| F— | Cl— | —(CH₂)₃— | Cl— |
| F— | Cl— | —(CH₂)₃— | CH₃— |
| F— | CH₃O— | —(CH₂)₂— | F— |
| F— | CH₃O— | —(CH₂)₅— | H— |
| F— | CH₃O— | —(CH₂)₃— | Cl— |
| F— | H— | —(CH₂)₃— | F— |
| Cl— | F— | —CH₂— | Cl— |
| Cl— | F— | —(CH₂)₃— | F— |
| Cl— | F— | —(CH₂)₃— | Cl— |
| Cl— | F— | —(CH₂)₃— | CH₃— |
| Cl— | H— | —(CH₂)₃— | F— |
| Cl— | H— | —(CH₂)₅— | F— |
| Cl— | Cl— | —(CH₂)₃— | F— |
| Cl— | CH₃O— | —(CH₂)₃— | F— |
| Cl— | CH₃O— | —(CH₂)₃— | CH₃— |
| Br— | H— | —(CH₂)₃— | F— |
| Br— | H— | —(CH₂)₃— | H— |
| Br— | H— | —(CH₂)₄— | F— |
| Br— | CH₃O— | —(CH₂)₂— | F— |
| Br— | CH₃O— | —(CH₂)₅— | F— |
| Br— | F— | —(CH₂)₃— | F— |
| Br— | Cl— | —(CH₂)₂— | F— |
| CH₃— | CH₃O— | —(CH₂)₃— | CH₃— |
| CH₃— | CH₃O— | —(CH₂)₅— | H— |
| CH₃— | F— | —(CH₂)₅— | F— |
| CH₃— | CH₃O— | —(CH₂)₃— | F— |
| CH₃— | CH₃O— | —(CH₂)₄— | F— |
| CH₃— | H— | —(CH₂)₃— | CH₃— |
| H— | CH₃O— | —(CH₂)₃— | F— |
| H— | CH₃O— | —(CH₂)₃— | Cl— |
| H— | F— | —(CH₂)₂— | CH₃— |
| H— | F— | —(CH₂)₅— | H— |
| H— | Cl— | —(CH₂)₃— | F— |
| H— | Cl— | —(CH₂)₅— | H— |

EXAMPLE 9

7-Fluoro-4-(p-fluorophenyl)-2-[4-(p-fluorophenyl)-4-hydroxypentyl]-1,2,3,4-tetrahydropyrrolo[3,4-b]indole hydrochloride (I: X and Z = F; A = —(CH₂)₃—; M = —C(CH₃)(OH)— and Y = F)

A methyl Grignard reagent prepared from 852 mg. (6 m moles) of methyl iodide and 144 mg. (6 m mole) of magnesium in 40 ml. of diethyl ether is divided into equal portions. To one-half is added portionwise 500 mg. (1.1 m moles) of 7-fluoro-4-(p-fluorophenyl)-2-[3-(p-fluorobenzoyl)propyl]-1,2,3,4-tetrahydropyrrolo[3,4-b]indole hydrochloride in 20 ml. of tetrahydrofuran, and the mixture allowed to stir for 1 hour. To the mixture is then added the other half of the Grignard solution, and stirring maintained for 30 min. The mix is poured into ice and water and extracted with ether. The combined ether extracts are dried over magnesium sulfate, concentrated to dryness, and the residue chromatographed on 20 g. of silica gel using 3:1 diethyl ether-ethanol as the eluate, each collecting fractions being 3 ml. Fractions 10–27 are combined and converted to the hydrochloride salt, 180 mg.

Mass Spectra M.: 450. Found: 450.

EXAMPLE 10

Starting with methyl magnesium iodide and the 4-aryl-2-benzoylalkyl-1,2,3,4-tetrahydropyrrolo[3,4-b]indoles of Examples 5 and 6 and employing the procedure of Example 9, the following congeners are prepared:

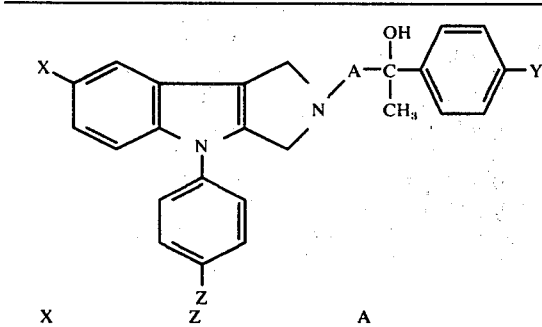

| X | Z | A | Y |
|---|---|---|---|
| F— | F— | —(CH$_2$)$_3$— | F— |
| F— | F— | —(CH$_2$)$_4$— | CH$_3$— |
| F— | F— | —(CH$_2$)$_4$— | Cl— |
| F— | Cl— | —(CH$_2$)$_3$— | F— |
| F— | Cl— | —(CH$_2$)$_3$— | Cl— |
| F— | Cl— | —(CH$_2$)$_3$— | CH$_3$— |
| F— | CH$_3$O— | —(CH$_2$)$_2$— | F— |
| F— | CH$_3$O— | —(CH$_2$)$_3$— | H— |
| F— | CH$_3$O— | —(CH$_2$)$_3$— | F— |
| F— | CH$_3$O— | —(CH$_2$)$_3$— | Cl— |
| F— | H— | —(CH$_2$)$_3$— | F— |
| Cl— | F— | —CH$_2$— | Cl— |
| Cl— | F— | —(CH$_2$)$_3$— | Cl— |
| Cl— | F— | —(CH$_2$)$_3$— | CH$_3$— |
| Cl— | H— | —(CH$_2$)$_3$— | F— |
| Cl— | H— | —(CH$_2$)$_3$— | F— |
| Cl— | Cl— | —(CH$_2$)$_3$— | F— |
| Cl— | CH$_3$O— | —(CH$_2$)$_3$— | F— |
| Cl— | CH$_3$O— | —(CH$_2$)$_3$— | CH$_3$— |
| Br— | H— | —(CH$_2$)$_3$— | F— |
| Br— | H— | —(CH$_2$)$_3$— | H— |
| Br— | H— | —(CH$_2$)$_4$— | F— |
| Br— | CH$_3$O— | —(CH$_2$)$_2$— | F— |
| Br— | CH$_3$O— | —(CH$_2$)$_3$— | F— |
| Br— | F— | —(CH$_2$)$_3$— | F— |
| Br— | Cl— | —(CH$_2$)$_3$— | F— |
| CH$_3$— | Cl— | —(CH$_2$)$_3$— | CH$_3$— |
| CH$_3$— | Cl— | —(CH$_2$)$_3$— | H— |
| CH$_3$— | F— | —(CH$_2$)$_3$— | F— |
| CH$_3$— | CH$_3$O— | —(CH$_2$)$_3$— | F— |
| CH$_3$— | CH$_3$O— | —(CH$_2$)$_4$— | F— |
| CH$_3$— | H— | —(CH$_2$)$_3$— | CH$_3$— |
| H— | CH$_3$O— | —(CH$_2$)$_3$— | F— |
| H— | CH$_3$O— | —(CH$_2$)$_3$— | Cl— |
| H— | F— | —(CH$_2$)$_2$— | CH$_3$— |
| H— | F— | —(CH$_2$)$_3$— | H— |
| H— | Cl— | —(CH$_2$)$_3$— | F— |
| H— | Cl— | —(CH$_2$)$_3$— | H— |

EXAMPLE 11

7-Fluoro-4-(p-fluorophenyl)-2-[4-(p-fluorophenyl)-4-acetoxybutyl]-1,2,3,4-tetrahydropyrrolo[3,4-b]indole

(I: X and Z=F; A=—(CH$_2$)$_3$—; M=—CH—wherein R$_1$=COCH$_3$ and Y=F).

Acetyl chloride (260 mg., 3.3 m moles) in 10 ml. of methylene chloride is added dropwise to a cold solution of 959 mg. (2.2m moles) of 7-fluoro-4-(p-fluorophenyl)-2-[4-(p-fluorophenyl)-4-hydroxybutyl]-1,2,3,4-tetrahydropyrrolo[3,4-b]indole in 30 ml. of methylene chloride containing 350 mg. (4.4 m mols) of pyridine. Following the addition, the reaction mixture is allowed to warm to room temperature and stir overnight. The mixture is decanted into a cold saturated aqueous sodium bicarbonate solution, and the crude product is extracted (3 × 50 ml.) with methylene chloride. The combined organic extracts are dried over magnesium sulfate and concentrated to an oil, which on chromatographing on a silica gel column, using 1:1 benzene-ethyl acetate as an elutate, provides the purified product.

EXAMPLE 12

Starting with the appropriate carbinol from Examples 7 through 10, and the requisite acid chloride or anhydride and employing the procedure of Example 11, the following esters are synthesized:

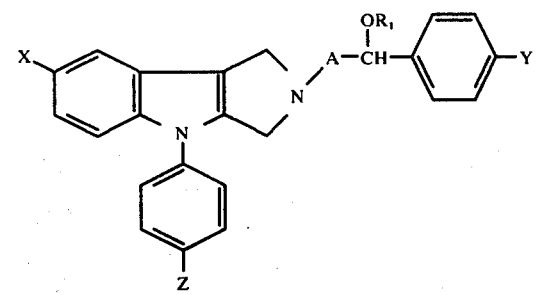

| X | Z | A | R$_1$ | Y |
|---|---|---|---|---|
| F— | CH$_3$O— | —(CH$_2$)$_3$— | CH$_3$CO— | F— |
| F— | F— | —(CH$_2$)$_3$— | CH$_3$CH$_2$CO— | F— |
| F— | F— | —(CH$_2$)$_3$— | (CH$_3$)$_3$CCO— | CH$_3$— |
| F— | F— | —(CH$_2$)$_3$— | CH$_3$CO— | Cl— |
| F— | F— | —(CH$_2$)$_4$— | CH$_3$CO— | F— |
| F— | Cl— | —(CH$_2$)$_3$— | CH$_3$(CH$_2$)$_2$CO— | Cl— |
| F— | H— | —(CH$_2$)$_3$— | CH$_3$CO— | F— |

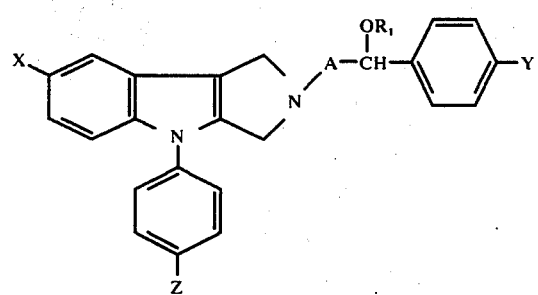

-continued

| X | Z | A | R₁ | Y |
|---|---|---|---|---|
| Cl— | F— | —(CH₂)₃— | (CH₃)₂CHCO— | F— |
| Cl— | F— | —CH₂— | CH₃(CH₂)₄CO— | Cl— |
| Cl— | H— | —(CH₂)₃— | CH₃CO— | F— |
| Cl— | H— | —(CH₂)₃— | (CH₃)₃CCO— | F— |
| Cl— | CH₃O— | —(CH₂)₃— | CH₃CH₂CO— | F— |
| Cl— | CH₃O— | —(CH₂)₃— | CH₃CO— | CH₃— |
| Cl— | Cl— | —(CH₂)₃— | CH₃CO— | F— |
| Cl— | Cl— | —(CH₂)₃— | CH₃(CH₂)₃CO— | F— |
| Br— | H— | —(CH₂)₄— | CH₃CO— | F— |
| Br— | CH₃O— | —(CH₂)₂— | (CH₃CH₂)₂CHCO— | F— |
| Br— | CH₃O— | —(CH₂)₃— | CH₃CH₂CH(CH₃)CO— | F— |
| Br— | F— | —(CH₂)₃— | CH₃CO— | F— |
| Br— | Cl— | —(CH₂)₂— | (CH₃)₂CHCH₂CO— | F— |
| CH₃— | Cl— | —(CH₂)₃— | CH₃CO— | H— |
| CH₃— | Cl— | —(CH₂)₃— | CH₃CO— | CH₃— |
| CH₃— | Cl— | —(CH₂)₃— | (CH₃)₃CCO— | CH₃— |
| CH₃— | F— | —(CH₂)₃— | CH₃(CH₂)₂CO— | F— |
| CH₃— | CH₃O— | —(CH₂)₃— | CH₃CO— | F— |
| CH₃— | CH₃O— | —(CH₂)₃— | CH₃CO— | F— |
| CH₃— | CH₃O— | —(CH₂)₄— | CH₃CH₂CO— | F— |
| CH₃— | H— | —(CH₂)₃— | CH₃CO— | CH₃— |
| CH₃— | H— | —(CH₂)₃— | (CH₃)₂CHCO— | CH₃— |
| H— | CH₃O— | —(CH₂)₃— | CH₃CO— | F— |
| H— | CH₃O— | —(CH₂)₃— | CH₃CO— | Cl— |
| H— | F— | —(CH₂)₂— | CH₃(CH₂)₄CO— | CH₃— |
| H— | F— | —(CH₂)₃— | CH₃(CH₂)₂CO— | H— |
| H— | Cl— | —(CH₂)₃— | CH₃CO— | H— |
| H— | Cl— | —(CH₂)₃— | CH₃CO— | F— |
| H— | Cl— | —(CH₂)₃— | CH₃CH₂CO— | F— |
| H— | Cl— | —(CH₂)₃— | (CH₃)₃CCO— | F— | and

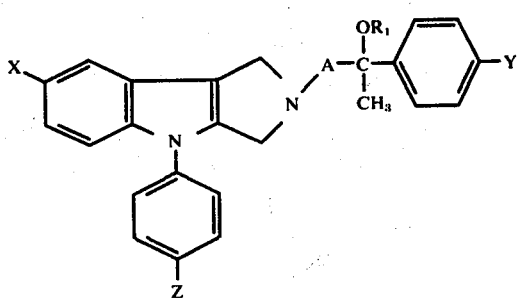

| X | Z | A | R₁ | Y |
|---|---|---|---|---|
| F— | F— | —(CH₂)₃— | CH₃CH₂CO— | F— |
| F— | F— | —(CH₂)₃— | (CH₃)₃CCO— | F— |
| F— | F— | —(CH₂)₄— | CH₃CO— | CH₃— |
| F— | Cl— | —(CH₂)₃— | CH₃CO— | Cl— |
| F— | CH₃O— | —(CH₂)₂— | (CH₃)₂CHCH₂CO— | F— |
| F— | CH₃O— | —(CH₂)₃— | CH₃CO— | H— |
| F— | H— | —(CH₂)₃— | CH₃CO— | F— |
| F— | H— | —(CH₂)₃— | (CH₃CH₂)₂CHCO— | F— |
| Cl— | F— | —CH₂— | CH₃CO— | Cl— |
| Cl— | F— | —(CH₂)₃— | CH₃CO— | Cl— |
| Cl— | F— | —(CH₂)₃— | CH₃(CH₂)₂CO— | CH₃— |
| Cl— | H— | —(CH₂)₃— | CH₃CO— | F— |
| Cl— | H— | —(CH₂)₃— | CH₃(CH₂)₂CO— | F— |
| Br— | H— | —(CH₂)₃— | (CH₃CH₂)₂CHCO— | F— |
| Br— | H— | —(CH₂)₄— | CH₃CH₂CO— | F— |
| Br— | CH₃O— | —(CH₂)₃— | CH₃CO— | F— |
| Br— | Cl— | —(CH₂)₂— | CH₃(CH₂)₂CO— | F— |
| CH₃— | Cl— | —(CH₂)₃— | CH₃CO— | CH₃— |
| CH₃— | Cl— | —(CH₂)₃— | CH₃CO— | H— |
| CH₃— | F— | —(CH₂)₃— | (CH₃)₃CCO— | F— |
| CH₃— | CH₃O— | —(CH₂)₃— | (CH₃)₃CCO— | F— |
| CH₃— | CH₃O— | —(CH₂)₄— | CH₃CO— | F— |
| CH₃— | H— | —(CH₂)₃— | CH₃CO— | CH₃— |
| H— | CH₃O— | —(CH₂)₃— | CH₃CH₂CH(CH₃)CO— | F— |
| H— | CH₃O— | —(CH₂)₃— | CH₃CO— | Cl— |
| H— | F— | —(CH₂)₂— | CH₃CO— | CH₃— |
| H— | F— | —(CH₂)₄— | (CH₃CH₂)₂CHCO— | H— |
| H— | Cl— | —(CH₂)₃— | CH₃CO— | F— |
| H— | Cl— | —(CH₂)₃— | CH₃(CH₂)₂CO— | F— |
| H— | Cl— | —(CH₂)₃— | CH₃(CH₂)₄CO— | F— |

EXAMPLE 13

7-Fluoro-4-(p-fluorophenyl)-2-(3,3-dimethyl-1-propyl)-1,2,3,4-tetrahydropyrrolo[3,4-b]indole hydrochloride (I: X and Z = F and R = —(CH₂)₂C(CH₃)₃).

A.

7-fluoro-4-(p-fluorophenyl)-2-t-butylacetyl-1,2,3,4-tetrahydropyrrolo[3,4-b]indole (V: X and Z = F and R' = —CH₂C(CH₃)₃)

To a suspension of 1.0 g. (3.7 m moles) of 7-fluoro-4-(p-fluorophenyl)-1,2,3,4-tetrahydropyrrolo[3,4-]indole in 10 ml. of methylene chloride is added t-butylacetyl chloride, prepared from 860 mg. of t-butylacetic acid and 10 ml. of thionyl chloride (C.A. 45, 1050g) in 10 ml. of the same solvent, and the mixture heated at steam bath temperatures for 30 min. The reaction mixture is treated with decolorizing charcoal, filtered and the filtrate concentrated under reduced pressure to 5 ml. The material which precipitates on cooling and scratching, mainly starting material, is filtered and dried, 231 mg., m.p. 159°–174° C. Dilution of the filtrate with ether causes the crude product to precipitate, 277 mg., m.p. 163°–174° C. Additional product is obtained by concentration of the ether filtrate to dryness, 403 mg., m.p. 170°–174° C.

The crude products are combined and employed in subsequent reactions without further purification.

B.

7-fluoro-4-(p-fluorophenyl)-2-(3,3-dimethyl-1-propyl)-1,2,3,4-tetrahydropyrrolo[3,4-b]indole hydrochloride (I: X and Z = F and R = —(CH₂)₂C(CH₃)₃).

To a suspension of 133 mg. (3.7 m moles) of lithium aluminium hydride in 5 ml. of dry tetrahydrofuran under a nitrogen atmosphere is added slowly 680 mg. (1.85 m moles) of 7-fluoro-4-(p-fluorophenyl)-2-t-butylacetyl-1,2,3,4-tetrahydropyrrolo[3,4-b]indole in 5 ml. of the same solvent. After 2 hrs. of stirring at room temperature the mixture is cooled in an ice bath and the reaction quenched by the dropwise addition of water. The tetrahydrofuran is removed in vacuo and the residue partitioned between water (25 ml.) and methylene chloride. The organic phase is separated, back-washed with water and a saturated brine solution and dried over sodium silfate. The residue remaining, after removal of the solvent under reduced pressure, is dissolved in ether, some insoluble filtered and diethyl ether saturated with hydrogen chloride carefully added to the ether. The precipitated hydrochloride is filtered and dried, 441 mg., m.p. 200°–208° C. Recrystallization from benzenemethylene chloride gives 166 mg. of the desired product, m.p. 222°–223° C.

Mass Spectra Calc'd M+ (free base): 355.
Found: 355.

Example 14

The procedure of Example 13 is repeated, starting with the requisite 4-aryl-1,2,3,4-tetrahydropyrrolo[3,4-b]indole and acid chloride, to give the following compounds:

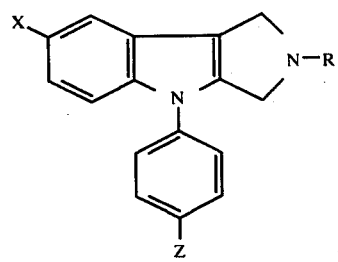

| X | Z | R |
|---|---|---|
| F— | F— | $C_2H_5$— |
| F— | F— | n-$C_3H_7$ |
| F— | Cl— | n-$C_5H_{11}$— |
| F— | $CH_3O$— | n-$C_4H_9$— |
| F— | H— | i-$C_4H_9$— |
| F— | Cl— | n-$C_6H_{13}$— |
| Cl— | F— | neo-$C_5H_{11}$— |
| Cl— | F— | $C_2H_5$— |
| $CH_3$— | H— | n—$C_5H_{11}$— |
| H— | $CH_3O$— | n—$C_3H_7$— |
| Br— | H— | $C_2H_5$— |
| Br— | F— | $C_2H_5$— |

EXAMPLE 15

7-Fluoro-4-(p-fluorophenyl)-2-benzyl-1,2,3,4-tetrahydropyrrolo[3,4-b]indole hydrochloride (I: X and Z = F and R = $C_6H_5CH_2$—)

A solution of 500 mg. (1.63 m moles) of 7-fluoro-4-(p-fluorophenyl)-1,2,3,4-tetrahydropyyrolo[3,4-b]indole, 418 mg. (2.44 m moles) of a α-bromotoluene and 526 mg. (4.08 m moles) of N,N-diisopropyl ethylamine in 5 ml. of toluene is heated to reflux for 30 min. Following a treatment with decolorizing charcoal, the solvent is removed in vacuo and the residue slurried in 25 ml. of ether. The ether solution is filtered and sufficient ether saturated with hydrogen chloride added to completely precipitate the product as the hydrochloride salt (pH 2–3). The crude product is filtered and dried 658 mg., m.p. 194°–202° C. The analytical sample is recrystallized from acetone-diethyl ether, m.p. 224°–226° C.

Anal. Calc'd for $C_{23}H_{18}N_2F_2$·HCl·⅛$H_2O$: C, 69.2; H, 4.9; N, 7.0.

Found: C, 69.2; H, 5.0; N, 6.9.

EXAMPLE 16

The procedure of Example 15 is repeated, starting with the appropriate alkylating agent and requisite 4-aryl-1,2,3,4-tetrahydropyrrolo[3,4-b]-indole, to provide the following analogs as the hydrochloride salt:

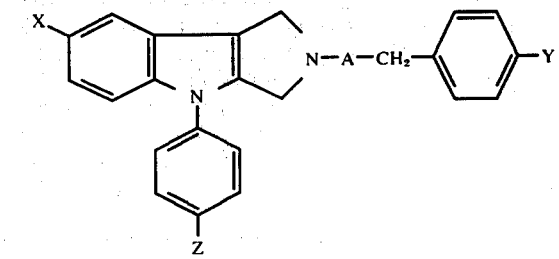

| X | Z | A | Y |
|---|---|---|---|
| F— | F— | —$CH_2$— | Cl— |
| F— | F— | —$CH_2$— | H— |
| F— | F— | —$(CH_2)_3$— | F— |
| F— | F— | —$(CH_2)_5$— | F— |
| F— | Cl— | —$CH_2$— | Cl— |
| F— | Cl— | —$(CH_2)_3$— | F— |
| F— | Cl— | —$(CH_2)_4$— | Cl— |
| F— | H— | —$(CH_2)_3$— | F— |
| Cl— | H— | —$CH_2$— | H— |
| Cl— | H— | —$(CH_2)_3$— | H— |
| Cl— | F— | —$(CH_2)_3$— | F— |
| Cl— | F— | —$(CH_2)_5$— | F— |
| Cl— | Cl— | —$CH_2$— | Cl— |
| Cl— | Cl— | —$CH_2$— | H— |
| Br— | Cl— | —$(CH_2)_4$— | Cl— |
| Br— | F— | —$(CH_2)_3$— | F— |
| Br— | F— | —$CH_2$— | H— |
| Br— | H— | —$CH_2$— | Cl— |
| $CH_3$— | H— | —$CH_2$— | H— |
| $CH_3$— | H— | —$(CH_2)_2$— | H— |
| $CH_3$— | H— | —$(CH_2)_3$— | F— |
| $CH_3$— | F— | —$(CH_2)_3$— | F— |
| $CH_3$— | F— | —$CH_2$— | H— |
| H— | F— | —$(CH_2)_3$— | F— |
| H— | F— | —$CH_2$— | F— |
| H— | F— | —$(CH_2)_4$— | Cl— |
| H— | Cl— | —$CH_2$— | H— |
| H— | Cl— | —$(CH_2)_3$— | F— |

EXAMPLE 17

7-Chloro-4-phenyl-2-i-propyl-1,2,3,4-tetrahydropyrrolo[3,4-b]indole hydrochloride (I: X = Cl; Z = H and R = i—$C_3H_7$-).

A.

7-chloro-2-i-propyl-1,2,3,4-tetrahydropyrrolo[3,4-b]indole.

A mixture of a 3.56 g. (0.02 mole) of p-chlorophenylhydrazine hydrochloride, 1.64 g. (0.02 mole) of sodium acetate and 2.54 g. (0.02 mole) of 1-isopropyl-3-pyrrolidinone in 35 ml. of water is allowed to stir for 2 hrs. The precipitated hydrazone is filtered, washed with water and dried.

To 2.82 g. (0.01 mole) of the above hydrazone is added 20 ml. of 85% phosphoric acid, and the resulting mixture allowed to stir for several hours, during which time the product precipitates from solution. The reaction is quenched in water, the pH adjusted to 7 with a dilute sodium hydroxide solution and the product filtered and dried.

B.
7-chloro-4-phenyl-2-i-propyl-1,2,3,4-tetrahydropyrrolo[3,4-b]indole hydrochloride A mixture of 7.8 g. (33.2 m moles) of 7-chloro-2-i-propyl-1,2,3,4-tetrahydropyrrolo[3,4-b]indole, 18.23 g. (0.116 mole) of bromobenzene, 10.4 g. (0.0364 mole) of cuprous bromide and 4.51 g. (0.0364 mole) of cuprous bromide and 4.51 g. (0.0364 mole) carbonate in 125 ml. of N-methyl-2-pyrrolidinone is heated under a nitrogen atmosphere at an internal temperature of 184° C. for 9 hrs. The mixture is cooled, decanted into 300 ml. of water containing 30 ml. of ethylene diamine and sodium chloride and extracted with benzene. The combined extracts are back-washed with a saturated brine solution, dried over magnesium sulfate and concentrated in vacuo.

The crude product is chromatographed on a silica gel column using methanol as an eluate and fractions of 5 ml. each. Elution of the product is followed by the thin layer chromatography, and the fractions containing the desired material are combined and concentrated under reduced pressure to dryness. The residual material is dissolved in ether and sufficient ether saturated with hydrogen chloride gas is added to precipitate the corresponding hydrochloride salt, which is further purified by recrystallization from ethyl acetate-ether.

EXAMPLE 18

Starting with the appropriately substituted phenylhydrazine and requisite 1-alkyl-3-pyrrolidinone and halobenzene, and employing the procedure of Example 17, the following 4-aryl-2-alkyl-1,2,3,4-tetrahydropyrrolo[3,4-b]-indoles are synthesized:

| X | Z | R |
|---|---|---|
| F— | F— | $(CH_3)_2CH—$ |
| F— | F— | $(CH_3)_3C—$ |
| F— | F— | $(CH_3CH_2)_2CH—$ |
| F— | $CH_3O—$ | $(CH_3)_2CH—$ |
| F— | Cl— | $CH_3(CH_3CH_2)CH—$ |
| F— | Cl— | $(CH_3)_3C—$ |
| Cl— | Cl— | $(CH_3)_3C—$ |
| Cl— | Cl— | $(CH_3)_2CH—$ |
| Cl— | F— | $(CH_3)_2CH—$ |
| Cl— | F— | $(CH_3CH_2)_2CH—$ |
| Cl— | H— | $CH_3(CH_3CH_2)CH—$ |
| Cl— | H— | $(CH_3)_3C—$ |
| Br— | $CH_3O—$ | $(CH_3)_3C—$ |
| Br— | $CH_3O—$ | $(CH_3CH_2)_2CH—$ |
| Br— | $CH_3O—$ | $(CH_3)CH—$ |
| Br— | F— | $(CH_3)CH—$ |
| $CH_3—$ | F— | $(CH_3)_2CH—$ |
| $CH_3—$ | F— | $(CH_3)_3C—$ |
| $CH_3—$ | $CH_3O—$ | $(CH_3CH_2)_2CH—$ |
| $CH_3—$ | $CH_3O—$ | $CH_3(CH_3CH_2)CH—$ |
| $CH_3—$ | Cl— | $(CH_3CH_2)_2CH—$ |
| H— | Cl— | $(CH_3)_3C—$ |
| H— | H— | $(CH_3)_3C—$ |
| H— | H— | $(CH_3)_2CH—$ |
| H— | F— | $(CH_3)_2CH—$ |
| H— | F— | $CH_3(CH_3CH_2)CH—$ |

EXAMPLE 19

7-Fluoro-4-(p-fluorophenyl)-2-[4-(p-fluorophenyl)-3-butenyl]-1,2,3,4-tetrahydropyrrolo[3,4-b]indole hydrochloride (I: X and Z = F; A = $—(CH_2)_2—$; M = $—CH=CH—$; and Y = F).

A solution of 1.9 g. (4.1 m moles) of 7-fluoro-4-(p-fluorophenyl)-2-[4-(p-fluorophenyl)-4-hydroxybutyl]-1,2,3,4-tetrahydropyrrolo[3,4-b]indole in 20 ml. of ethanol and 50 ml. of 6N hydrochloric acid is heated to reflux for 4 hrs., and is then allowed to stir at room temperature for several days. The precipitated product is filtered and dried. Further purification is effected by reprecipitation from methanol using diethyl ether.

EXAMPLE 20

Starting with the carbinols of Examples 7 and 8, and employing the procedure of Example 19, the following pyrrolo[3,4-b]indoles are prepared:

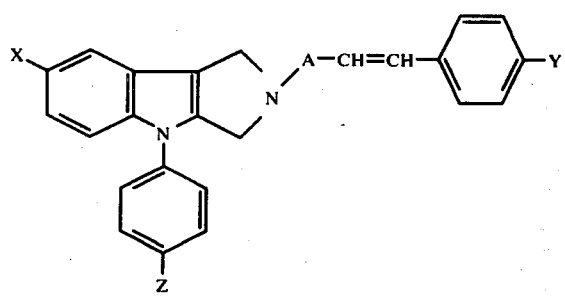

| X | Z | A | Y |
|---|---|---|---|
| F— | $CH_3O—$ | $—(CH_2)_2—$ | F— |
| Cl— | F— | $—(CH_2)_2—$ | F— |
| F— | F— | $—(CH_2)_2—$ | $CH_3—$ |
| F— | F— | $—(CH_2)_2—$ | Cl— |
| F— | F— | $—CH_2—$ | F— |
| F— | F— | $—(CH_2)_2—$ | F— |
| F— | F— | $—(CH_2)_2—$ | H— |
| F— | F— | $—(CH_2)_3—$ | F— |
| F— | F— | $—(CH_2)_4—$ | F— |
| Cl— | Cl— | $—CH_2—$ | F— |
| Cl— | $CH_3O—$ | $—CH_2—$ | F— |
| Cl— | $CH_3O—$ | $—CH_2—$ | Cl— |
| Br— | H— | $—CH_2—$ | F— |
| Br— | H— | $—(CH_2)_2—$ | F— |
| Br— | $CH_3O—$ | $—(CH_2)_3—$ | F— |
| Br— | $CH_3—$ | $—CH_2—$ | F— |
| $CH_3—$ | Cl— | $—CH_2—$ | $CH_3—$ |
| $CH_3—$ | Cl— | $—(CH_2)_3—$ | H— |
| $CH_3—$ | F— | $—(CH_2)_4—$ | F— |
| $CH_3—$ | $CH_3O—$ | $—CH_2—$ | F— |
| $CH_3—$ | H— | $—CH_2—$ | $CH_3—$ |
| H— | $CH_3O—$ | $—CH_2—$ | F— |
| H— | $CH_3O—$ | $—CH_2—$ | Cl— |
| H— | F— | $—(CH_2)_3—$ | H— |
| H— | Cl— | $—(CH_2)_3—$ | H— |

EXAMPLE 21

Test Procedures and Results

The effects of the compounds of the present invention on prominent amphetamine-induced symptoms were studied in rats by a rating scale modeled after the one reported by Quinton and Halliwell; and Weissman. Groups of five rats were placed in a covered plastic cage measuring approximately 26 cm. × 42 cm. × 16 cm. After a brief period of acclimation in the cage, the rats in each group were treated intraperitoneally (i.p.) with the test compound. They were then treated 1, 5 and 24 hrs. later with d-amphetamine sulfate, 5 mg./kg., i.p. One hour after amphentamine was given each rat was observed for the characteristic amphetamine behavior of moving around the cage. On the basis of dose-response data after amphetamine it was possible to determine the effective dose of the compound necessary to antagonize or block the characteristic amphetamine behavior of cage movement for fifty percent of the rats tested ($ED_{50}$). The time of rating chosen coincides with the peak action of amphetamine which is 60–80 min. after treatment with this agent.

Employing the above-described procedure, the following compounds were tested for their ability to block the behavior effects to amphetamine, the results being reported as the $ED_{50}$ in mg./kg. at the indicated times:

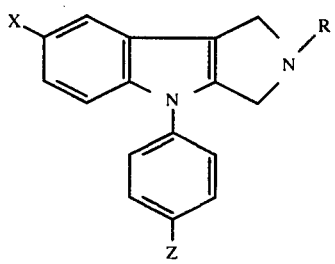

| X | Z | R | $ED_{50}$; mg./kg. | | |
|---|---|---|---|---|---|
| | | | 1 hr. | 5 hrs. | 24 hrs. |
| F | F | $CH_3$ | 3.2–5.6 | >10 | — |
| F | F | OH<br>|<br>p—$FC_6H_4CH(CH_2)_3$— | 1–3.2 | 1–3.2 | — |
| chlorpromazine | | | >10 | | |

EXAMPLE 22

8-Chloro-4-(p-fluorophenyl)-2-[4-(p-fluorophenyl)-4-hydroxybutyl]-1,2,3,4-tetrahydropyrrolo[3,4-b]indole acetate Five grams of 8-chloro-4-(p-fluorophenyl)-2-[4-(fluorophenyl)-4-hydroxybutyl]-1,2,3,4-tetrahydropyrrolo[3,4-b]indole hydrochloride in 75 ml. of water is treated with 3 ml. of water containing 1.0 g. of sodium hydroxide, and the liberated free base extracted into 150 ml. of diethyl ether. The ether layer is separated, dried over magnesium sulfate and treated with 1 ml. of glacial acetic acid. The organic solvent and excess acetic acid are removed under reduced pressure and the residue triturated with hexane and filtered.

In a similar manner, other acid addition salts, especially those which are pharmaceutically acceptable, can be prepared.

EXAMPLE 23

Tablets

A tablet base is prepared by blending the following ingredients in the proportion by weight indicated:

| Sucrose, U.S.P. | 80.3 |
|---|---|
| Tapioca Starch | 13.2 |
| Magnesium stearate | 6.5 |

Into this tablet base there is blended sufficient 8-fluoro-4-(p-fluorophenyl)-2-[4-(p-fluorophenyl)-4-hydroxybutyl]-1,2,3,4-tetrahydroprrolo-[3,4-b]indole hydrochloride to provide tablets containing 2.0, 5.0, 10.0 and 20.0 mg. of active ingredient per tablet. The composition are each compressed into tablets, each weighing 360 mg., by conventional means.

EXAMPLE 24

Capsules

A blend is prepared containing the following ingredients:

| Calcium carbonate, U.S.P. | 17.6 mg. |
|---|---|
| Dicalcium phosphate | 18.8 mg. |
| Magnesium trisilicate, U.S.P. | 5.2 mg. |
| Lactose, U.S.P. | 5.2 mg. |
| Potato starch | 5.2 mg. |
| Magnesium stearate A | 0.8 mg. |
| Magnesium stearate B | 0.35 mg. |

To this blend is added sufficient 8-chloro-4-(p-fluorophenyl)-2-[4-(p-fluorophenyl)-4-hydroxybutyl]-1,2,3,4-tetrahydropyrrolo[3,4-b]indole hydrochloride to provide capsules containing 2.0, 5.0, 10.0 and 20.0 mg. of active ingredient per capsule. The compositions are filled into hard gelatin capsules in the amount of 350 mg. per capsule.

EXAMPLE 25

Suspension

A suspension of 8-fluoro-4-(p-fluorophenyl)-2-[4-(p-tolyl)-4-hydroxybutyl]-1,2,3,4-tetrahydropyrrolo[3,4-b]indole sulfate is prepared with the following composition:

| Effective ingredient | g. | 25.00 |
|---|---|---|
| 70% Aqueous sorbitol | g. | 741.29 |
| Glycerine, U.S.P. | g. | 185.35 |
| Gum acacia (10% solution) | ml. | 100.00 |
| Polyvinylpyrrolidone | g. | 0.50 |
| Distilled water, sufficient to make 1 liter | | |

To this suspension, various sweeteners and flavorants are added to improve the platability of the suspension. The suspension contains approximately 25 mg. of effective agent per milliliter.

EXAMPLE 26

Injectable Preparation

Sesame oil is sterilized by heating to 120° C. for 2 hrs. To this oil a sufficient quantity of pulverized 8-fluoro-4-(p-fluorophenyl)-2-[4-(p-fluorophenyl)-4-hydroxybutyl]-1,2,3,4-tetrahydropyrrolo[3,4-b]indole hydrochloride to make a 0.025% suspension by weight. The solid is thoroughly dispersed in the oil by use of a colloid mill. It is then filtered through a 100 to 250 mesh screen, poured into sterile vials and sealed.

What is claimed is:
1. A compound selected from those of the formula

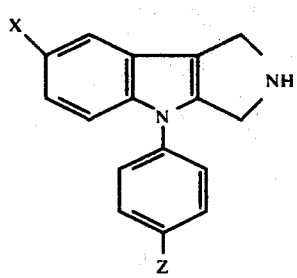

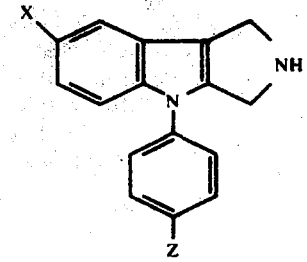

wherein X is selected from the group consisting of fluoro, chloro, bromo, methyl and hydrogen; and Z is selected from the group consisting of fluoro, chloro, methoxy and hydrogen.
2. A compound of claim 1 wherein X is fluoro.
3. The compound of claim 2 wherein Z is fluoro.

wherein X is selected from the group consisting of fluoro, chloro, bromo, methyl and hydrogen; and Z is selected from the group consisting of fluoro, chloro, methoxy and hydrogen.
2. A compound of claim 1 wherein X is fluoro.
3. The compound of claim 2 wherein Z is fluoro.

* * * * *

UNITED STATES PATENT OFFICE
CERTIFICATE OF CORRECTION

Patent No. 4,006,164　　　　　　　Dated February 1, 1977

Inventor(s) Willard H. Welch, Jr., et al.

It is certified that error appears in the above-identified patent and that said Letters Patent are hereby corrected as shown below:

Column 2, line 15, "preset" should read -- present --.

Column 9, line 52, "-Ch=CH-" should read -- -CH=CH- --.

Column 17, line 21, "M.:" should read -- $M^+$: -- .

Column 18, line 60, cancel redundant formula.

Column 19, line 60, cancel redundant formula.

Column 21, line 3, "$M^+$" should read -- $M^+$ --.

Column 23, line 9, "cuprous bromide and 4.51 g. (0.0364 mole)" should read -- sodium --.

Column 23, line 20, cancel "the" before "thin".

Column 25, line 44, "(fluorophenyl)-" should read -- (p-fluorophenyl)- --.

UNITED STATES PATENT OFFICE
CERTIFICATE OF CORRECTION

Patent No. 4,006,164  Dated February 1, 1977

Inventor(s) Willard H. Welch, Jr., et al.

It is certified that error appears in the above-identified patent and that said Letters Patent are hereby corrected as shown below:

Column 26, line 3, "tetrahydroprrolo-" should read -- tetrahydropyrrolo --.

Column 26, line 6, "composition" should read -- compositions --.

Column 28, lines 1-16, omit everything in column 28.

Signed and Sealed this fifth Day of July 1977

[SEAL]

Attest:

RUTH C. MASON
Attesting Officer

C. MARSHALL DANN
Commissioner of Patents and Trademarks